United States Patent [19]

McConnell

[11] 4,185,631
[45] Jan. 29, 1980

[54] READILY REMOVABLE EXPANDING CATAMENIAL TAMPON

[75] Inventor: Wesley J. McConnell, Somerset Township, Somerset County, N.J.

[73] Assignee: Johnson & Johnson

[21] Appl. No.: 887,698

[22] Filed: Mar. 17, 1978

[51] Int. Cl.² ............................................ A61F 13/20
[52] U.S. Cl. ..................................... 128/285; 128/270
[58] Field of Search ................. 128/270, 285, 127, 263

[56] References Cited

U.S. PATENT DOCUMENTS

| | | | |
|---|---|---|---|
| 3,766,921 | 10/1973 | Dulle | 128/263 |
| 3,794,029 | 2/1974 | Dulle | 128/270 |
| 3,946,737 | 7/1974 | Kobler | 128/285 |
| 4,018,225 | 4/1977 | Elmi | 128/285 |

FOREIGN PATENT DOCUMENTS

| | | | |
|---|---|---|---|
| 565553 | 8/1975 | Switzerland | 128/270 |
| 712456 | 7/1954 | United Kingdom | 128/270 |

Primary Examiner—Robert W. Michell
Assistant Examiner—C. W. Shedd
Attorney, Agent, or Firm—Jason Lipow

[57] ABSTRACT

A catamenial tampon is provided for precluding the bypass of menstrual fluid in use while simultaneously being easy to remove after use. The tampon comprises a generally cylindrical absorbent body having a ring slidably engaged around the body, the ring also being attached to the insertion end of the absorbent body. The ring comprises material which will expand when in place within the vagina to preclude menstrual fluid bypass. A withdrawal string is attached to the cylindrical body whereby, when the tampon is being removed by force exerted on the cylindrical body by means of the withdrawal string, the cylindrical body is disengaged from the ring and removed from the tampon followed by the attached ring.

7 Claims, 6 Drawing Figures

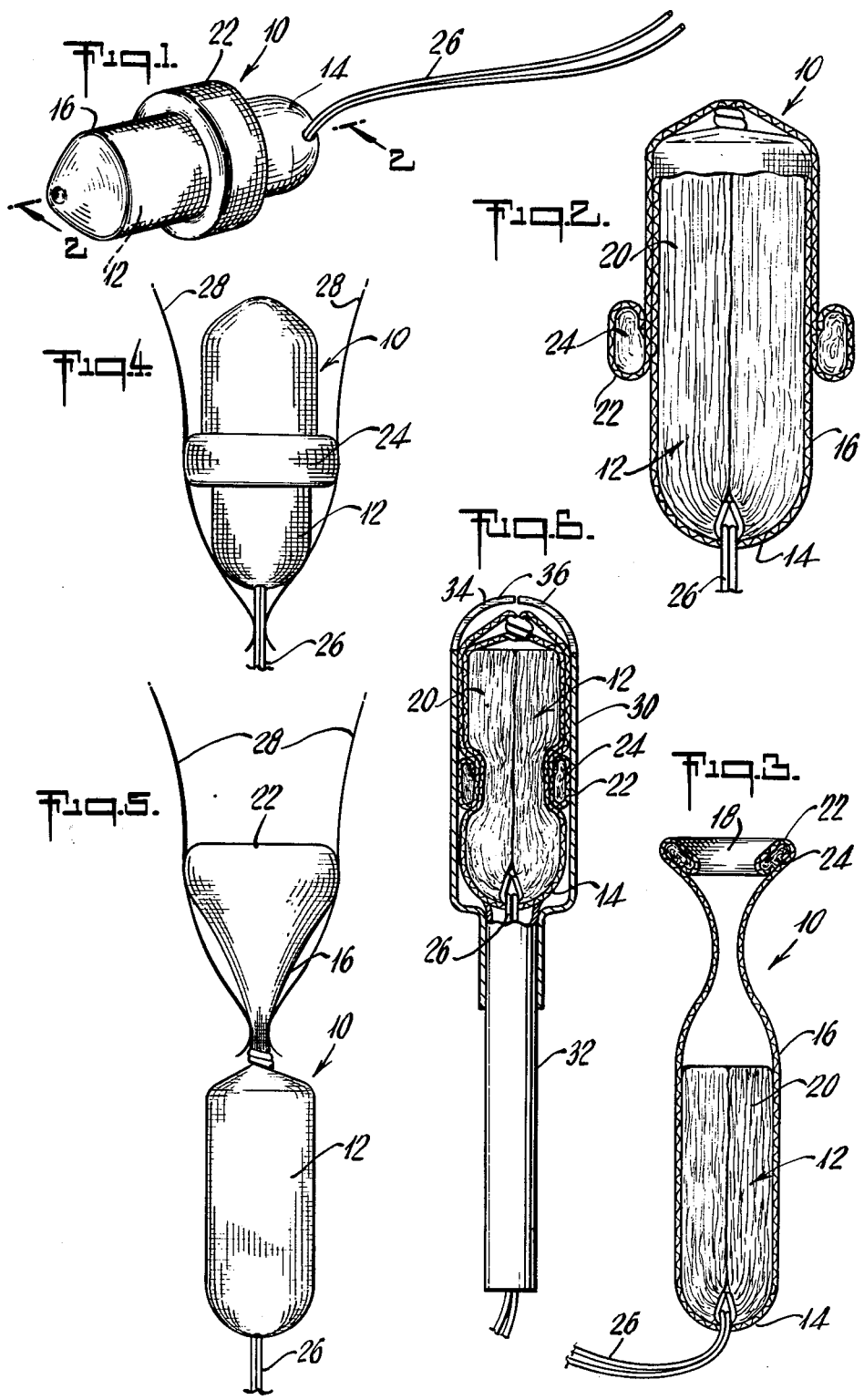

READILY REMOVABLE EXPANDING CATAMENIAL TAMPON

BACKGROUND OF THE INVENTION

This invention concerns catamenial tampons and, in particular, concerns improvements in such tampons to prevent menstrual fluid bypass.

The art is now replete with suggestions for catamenial tampons designed to be inserted into the vagina during menstruation and to preclude the passage of menstrual fluid by blocking the vaginal passage and absorbing menses. The vast majority of tampons now in use consist of highly compressed absorbent bodies which upon insertion into the vaginal vault, expand and purportedly seal the vagina against fluid bypass. Expansion is accomplished in several alternative ways. Most commonly, the tampons are comprised of absorbent materials which when contacted with menstrual fluid absorb and swell, thus increasing the size of the tampons. These tampons usually consist of compressed cellulosic fibers or synthetic materials, such as hydrophilic foams, which expand when wet.

Alternatively, suggestions have been made for providing the tampon with mechanical means for expansion. An example of this is disclosed in U.S. Pat. No. 3,706,311 issued to Daniel D. Kokx et al. on Dec. 19, 1972.

Irrespective of the method chosen, all of these prior tampons suffer from a common problem. While they are generally small enough to be inserted into the vaginal vault comfortably through the introitus, they all are intentionally designed to increase greatly in cross-section once emplaced within the vagina. Having been so inserted and having performed the intended function of absorbing and blocking menstrual fluid, the problem now remains to remove the now enlarged tampon from the vagina through the relatively narrow vaginal introitus. This must be accomplished without discomfort to the user and without exerting a compressive force on the tampon sufficient to squeeze out menstrual fluid retained in the tampon.

Heretofore, this problem has not been satisfactorily solved and so a need remains for a catamenial tampon capable of being inserted comfortably and then expanding to block menstrual fluid bypass when in the vaginal vault and, at the same time, capable of being removed after such expansion without discomfort and without giving up the absorbed menses.

SUMMARY OF THE INVENTION

In accordance with this invention, a tampon is provided which comprises an absorbent body for insertion into the vagina consisting of a generally cylindrical shape having a withdrawal end and an insertion end. An annular ring of absorbent material is fixed around the absorbent body, the ring being slidably engaged around the absorbent body and having means of attachment to the insertion end of the absorbent body. A withdrawal string is affixed to the withdrawal end of the tampon.

In use, the tampon may be inserted into the vagina and the expandable ring, once in the vagina, will expand to act as a seal and preclude menstrual bypass. Having used the tampon, the user may then remove the same by exerting force on the withdrawal string. Because of the sliding relationship between the cylindrical absorbent body and the ring, the forces exerted on the withdrawal string will cause the cylindrical body to slide out of the ring and be first removed from the vagina. Once the absorbent cylindrical body is removed therefrom, the ring will tend to collapse, and being attached to the cylindrical body, will follow the body out of the vagina. Because the ring tends to collapse, the user will suffer no discomfort notwithstanding the fact that the tampon in use had a large external diameter.

In a preferred embodiment, both the ring and the cylindrical body are enveloped in an elongated sack or envelope of a menstrual fluid pervious material. The cylindrical body is placed near the bottom of the sack and the ring is placed in a hem portion at the open mouth of the sack. The sack is then twisted about the insertion end of the cylindrical body and then the upper portion is rolled down over the cylindrical body with the hemmed in ring being slipped over the enclosed cylindrical body.

BRIEF DESCRIPTION OF THE DRAWINGS

In the drawings:

FIG. 1 is a perspective view of a tampon embodying the teachings of this invention, shown as it would be upon insertion;

FIG. 2 is a cross-sectional view of the tampon of FIG. 1, taken along line 2—2;

FIG. 3 is a cross-sectional view of the tampon of FIGS. 1 and 2 shown in a position prior to having the expanding ring folded over the cylindrical body;

FIG. 4 is a schematic illustration of the tampon of this invention emplaced in the vagina;

FIG. 5 is a schematic illustration of the tampon of this invention as it is removed from the vagina; and FIG. 6 illustrates in cross-sectional view, the tampon of this invention in a tampon application.

DETAILED DESCRIPTION OF THE INVENTION

Referring now to FIGS. 1, 2 and 3, illustrated therein is a tampon 10 which represents a preferred embodiment of this invention. The tampon 10 comprises a generally cylindrical absorbent body 12 which can be constructed of a wide variety of absorbent materials now known such as, for example, cellulose fibers including cotton, wood pulp, regenerated cellulose or the like; chemically modified cellulose, starch or other polysaccharides including, for example, polysaccharide ethers or esters such as carboxyalkyl polysaccharides, grafted cellulose copolymers and homopolymers such as cellulose having poly(acrylate) or poly(acrylate-ethyl acrylate) copolymer grafted to the polysaccharide backbone. Some of these absorbents may be rendered insoluble and/or more absorbent by virtue of being crosslinked or by having additional polymer moieties grafted thereto. In addition to such polysaccharides, certain synthetically produced absorbents may be employed, e.g., polyurethane or polyester foams which have been treated so as to be hydrophilic or polyacrylamide having chemically bonded thereto hydrophilic groups. Many other suitable absorbent materials, as will occur to one skilled in the art, may also be employed.

The absorbent material may be compressed into a relatively rigid cylindrical body, this being the preferred form when the tampon is designed to be inserted digitally. Since it is within the contemplation of this invention that the tampon may also be inserted by means of a tampon applicator, the absorbent can also be in a non-rigid form as, for example, when using a non-rigid polyurethane foam. Further, the absorbent may take various forms such as powders, fibers, flakes or other shapes. In the case of foams, these may be molded into a cylindrical shape or may be used in the form of discrete particles of foam.

In the preferred embodiment illustrated in the drawings, the cylindrical absorbent body 12 is positioned in the closed bottom 14 of a menstrual fluid pervious sack 16. The sack may be constructed of either a woven material which is pervious to menstrual fluid such as, for example, gauze or may be made of a non-woven material. As is best viewed in FIG. 3, the open mouth 18 of the sack 16 extends well above the insertion end 20 of the cylindrical body 12.

At the open mouth 18 of sack 16, a hem 22 is provided around the periphery of the mouth for enclosing a ring 24 of expandable material. The ring 24 is expandable in the sense that when the tampon is emplaced within the vaginal vault, the ring will increase in diameter to occlude the vaginal passage and prevent menstrual fluid bypass. This may be accomplished by constructing the ring of a material which is resilient and maintaining the ring in a compressed condition prior to insertion. Such a construction is particularly applicable for tampons of this invention which employ applicators for insertion as contrasted with digital insertion methods. A material of this kind would be a resilient foam, for example, polyurethane foam.

Alternatively, the ring 24 may be comprised of a material which will expand when wetted with menstrual fluid. Such a material could be any of those described in connection with the cylindrical body 12. A material of this type is best suited for a digitally inserted tampon.

Irrespective of which material is used for the ring 24, referring particularly to FIGS. 2 and 3, the portion of the sack 16 is closed off at the top of the cylindrical body 12 (at the insertion end). This best accomplished by simply twisting the sack closed at this point. As is shown in FIG. 2, the portion of the sack extending above the now enclosed cylindrical body 12 is rolled over the cylindrical body 12 so that the ring 24 is engaged about the cylindrical body. The interpositioning of the layers of sack between the cylindrical body and the ring insure that the ring is slidable on the cylindrical body and can be disengaged with little effort. It should be noted that while the ring can slide out of engagement with the cylindrical body, it is constrained by the sack from doing so completely in the direction toward the bottom of the cylindrical body (opposite the insertion end). Similarly, while the ring may be completely disengaged from the cylindrical body in the direction toward the top of the body, it will still remain attached to the tampon as a whole, by virtue of the sack.

In accordance with methods well known in the art, the bottom of the tampon 10 is provided with a removal string 26 for withdrawing the tampon after use. Such string may simply be adhered to the sack alone or may be pierced through the cylindrical body, as is illustrated in the drawings.

Referring now to FIG. 4, schematically illustrated therein is a cross-sectional view of the tampon 10 of this invention, employed within the vagina. As is illustrated, the ring 24 has expanded to fill the vaginal passageway and seal against the vaginal walls 28. In this manner, menses bypass is precluded. As has been described above, if the tampon in this expanded state were to be removed from the vagina without changing the tampon configuration, the user would suffer great discomfort. In accordance with the teachings of this invention however, the ring 24 is slidably engaged over the cylindrical body 12 of the tampon. Accordingly, referring to FIG. 5, as the tampon is removed after use by means of withdrawal string 26, the cylindrical body 12 slides out of engagement with the ring 24, the ring being retarded in its movement by the frictional restraint exerted on it by the vaginal walls. Accordingly, the cylindrical body is first removed from the vagina. The ring 24, being attached to the insertion end of the cylindrical body by virtue of the sack 16, will follow and be removed after the cylindrical body. This removal of the ring 24 occurs, however, only after the cylindrical body has been disengaged and so the ring is now capable of collapsing on itself and will present no discomfort to the user upon removal.

While FIG. 1 has illustrated an embodiment of the tampon of this invention which is suitable for digital insertion, as has been stated above, the invention likewise applies to tampons inserted by means of applicators. FIG. 6 illustrates in cross section, the tampon 10 of this invention fitted into a typical tampon applicator. Such applicator comprises a first generally cylindrical tampon retainer 30 and a plunger 32 designed to telescope within the retainer and expel the tampon 10 through the insertion end 34. As is illustrated, this insertion end is provided with closed petals 36 which will open when the tampon is expelled to allow emplacement of the tampon within the vagina. The ring 24, has been compressed to fit within the tampon retainer and accordingly, it is preferable for use in applicators that the ring be chosen of a resilient material such as, for example, compressible foam.

It will be understood that while this invention has been described in terms of specific embodiments such as those depicted in the drawings, many other variations are to be considered within the scope of the invention. For example, the ring 24 illustrated in the drawings is relatively small and engages only a small area of the cylindrical body. It is apparent, however, that the ring could be made substantially higher so as to engage a larger portion or even a major portion of the cylindrical body. Even the ultimate extreme, the cylindrical body totally engaged by the ring, is possible.

Similarly, the means for attachment of the ring to the cylindrical body has been shown in the drawings as a menstrual fluid pervious sack. It will be clear to those skilled in the art that many alternative means for attachment are possible including, for example, tapes, strings or other extentions from the ring which are affixed to the cylindrical body.

What is claimed is:

1. A catamenial tampon comprising an absorbent, generally cylindrical body having an insertion end and a withdrawal end;

an annular ring slidably engaged around the absorbent body, said ring comprising a material which expands when emplaced within the vagina; and means for attachment of said ring to the insertion end of said absorbent body, said means comprising a menstrual fluid pervious elongated sack having a closed end at the bottom portion thereof and an open mouth at the top portion, said cylindrical body being placed in the bottom portion, said sack being closed off about the insertion end of said cylindrical body with the top portion of the sack extending above the insertion end, said ring being affixed to the periphery of said open mouth of the sack and said ring and said top portion of the sack being rolled over the cylindrical body to slidably engage the ring about the cylindrical body;

said tampon being provided with a withdrawal string affixed to the cylindrical body for removing said tampon from the vagina after use.

2. The tampon of claim 1 wherein said ring expands when wetted with menstrual fluid.

3. The tampon of claim 1 wherein said ring comprises a compressed absorbent material.

4. The tampon of claim 1 wherein said ring comprises a compressed, resilient material and means are provided for inserting said ring, in the compressed state, into the vagina and for releasing said ring from compression after insertion.

5. The tampon of claim 4 wherein said means for inserting comprise a tampon applicator wherein said tampon is held during insertion in a tampon retainer which maintains said ring in the compressed state during insertion.

6. The tampon of claim 4 wherein said ring comprises a resilient foam.

7. The tampon of claim 6 wherein said foam is polyurethane.

* * * * *